(12) United States Patent
Cui et al.

(10) Patent No.: US 6,541,506 B1
(45) Date of Patent: Apr. 1, 2003

(54) ANTIFUNGAL ENEDIYNES

(75) Inventors: Baoliang Cui, Westboro, MA (US); James Bruce McAlpine, Bolton, MA (US); Maureen Kelly Talbot, Shrewsbury, MA (US); Shu-Wei Yang, Worcester, MA (US); Catherine Heintz, Sheffield (GB); Angela Stafford, Castleton (GB)

(73) Assignee: Phytera Incorporated, Worcester, MA (US)

( * ) Notice: Subject to any disclaimer, the term of this patent is extended or adjusted under 35 U.S.C. 154(b) by 0 days.

(21) Appl. No.: 09/679,672

(22) Filed: Oct. 5, 2000

Related U.S. Application Data

(60) Provisional application No. 60/158,099, filed on Oct. 7, 1999.

(51) Int. Cl.[7] ........................ C07D 307/54; A01N 43/08
(52) U.S. Cl. ........................ 514/428; 514/435; 514/461; 548/562; 549/79; 549/499
(58) Field of Search ............................ 548/562; 547/79, 547/499; 514/428, 438, 461

(56) References Cited

U.S. PATENT DOCUMENTS

| | | | |
|---|---|---|---|
| 3,919,260 A | 11/1975 | Hejno et al. |
| 4,923,884 A | 5/1990 | Chandraratna |
| 4,958,037 A | 9/1990 | Floyd, Jr. |
| 5,399,724 A | 3/1995 | Takayanagi et al. |

*Primary Examiner*—Robert Gerstl
(74) *Attorney, Agent, or Firm*—Clark & Elbing LLP

(57) ABSTRACT

The invention features enediynes and methods for their production and use. The enediynes of the invention have the formula:

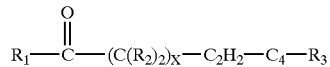

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

30 Claims, 2 Drawing Sheets

Scheme 1

Scheme 2

Scheme 3

ANTIFUNGAL ENEDIYNES

CROSS-REFERENCE TO RELATED APPLICATIONS

This application claims benefit from U.S. provisional patent application Ser. No. 60/158,099, filed Oct. 7, 1999 (now pending), hereby incorporated by reference.

BACKGROUND OF THE INVENTION

The invention relates to compounds useful in inhibiting fungal infections.

Fungal infections (mycoses) can contribute to and complicate many diseases, including pulmonary diseases and respiratory tract diseases. The number of instances of opportunistic fungal infections have increased, particularly in immunocompromised patients, such as those with AIDS, those undergoing chemotherapy for cancer, and those undergoing therapy to prevent graft rejection following organ transplant surgery.

In animals, fungal infections may be cutaneous, subcutaneous, or systemic. Superficial mycoses include tinea capitis, tinea corporis, tinea pedis, onychomycosis (e.g., nail fungus), perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis, paracoccidioidomycosis, North American blastomycosis, histoplasmosis, coccidioidomycosis, and sporotrichosis.

Plants are also susceptible to fungal infections. Plant diseases are caused by a myriad of invasive fungal pathogens which fall into many genera, for example: soft rot (e.g., Rhizopus spp.), leaf curl (e.g., Taphrina spp.), powdery mildew (e.g., Sphaerotheca spp.), leaf spots (e.g., Fulvia spp.), blight (e.g., Alternaria spp.), blast (e.g., Magnaporthe spp.), black rot (e.g., Guignardia spp.), scab (e.g., Venturia spp.), wilts (e.g., Fusarium spp.), rusts (e.g., Puccinia spp.), smuts (e.g., Ustilago spp.), and cankers (e.g., Rhizoctonia spp.).

Examples of pathogenic organisms include dermatophytes (e.g., *Microsporum canis, M. gypseum, M. distortum, M. audouinii, M. ferrugineum, M. rivalieri, M. fulvum, M. cookei, M. vanbreuiseghemii, M. persicolor, Trichophyton rubrum, T. mentagrophytes, T. mengninii, T. nanum, T. schoenleinii, T. tonsurans, T. verrucosum, T. soudanense, T. violaceum, T. yaoundei, T. gourvilii, T. simii, T. ajelloi, Hendersonula toruloidea*), yeasts (e.g., *Candida albicans, C. tropicalis*), *Torulopsis glabrata, Epidermophyton floccosum, Malassezia furfur* (*Pityropsporon orbiculare, P. ovale*), *Cryptococcus neoformans, Aspergillus fumigatus* and other *Aspergillus* spp., Zygomycetes (e.g., Rhizopus, Mucor), *Paracoccidioides brasiliensis, Blastomyces dermatitidis, Histoplasma capuslatum, Coccidioides immitis*, and *Sporothrix schenckii*.

SUMMARY OF THE INVENTION

In one aspect, the invention features a substantially pure compound having the formula:

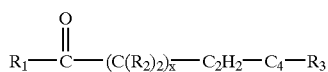

(I)

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive. In all of the compounds of the invention (Compounds I-V), the sum of the carbons on the $R_2$ moieties is preferably less than 15. More preferably, the sum of the carbons on the $R_2$ moieties is less than 9 and, most preferably, less than 5. Most preferably, each $R_2$ is H or, alternatively, each $R_2$ is, independently, H, $CH_3$, or $C_2H_5$. In other preferred embodiments, $R_3$ is a furan ring, and X is an integer between 5 and 7, inclusive. The claimed compounds are capable of inhibiting the growth of a fungal cell (e.g., a species of Candida or a dermatophyte). The compounds of the invention can be admixed with a pharmaceutically acceptable carrier to produce a pharmaceutical composition. In one preferred example, the composition is formulated for topical application.

In another aspect, the invention features a substantially pure compound having the formula:

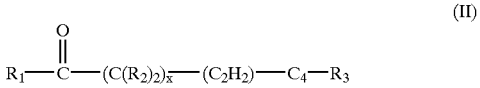

(II)

wherein $R_1$ is OH, $NH_2$, $OCH_3$, or $OC_2H_5$; $R_3$ is a pyrrole, furan, or thiophene ring; and X is an integer between 5 and 7, inclusive. In preferred compounds, $R_1$ is OH and/or $R_3$ is a furan ring. These compounds also can be provided as pharmaceutically acceptable compositions and used to inhibit the growth of fungal cells, e.g., to treat fungal infections in plants and animals, including humans. Preferably, the compound inhibits growth of fungal cells by at least 25%, more preferably by at least 50%, and most preferably by at least 90%, as determined by a standard assay described herein.

The compounds of the invention, in addition to being useful for treating fungal infections, can be used for preventing fungal infections.

Preferred compounds of within formula (II) have the formula:

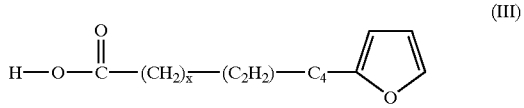

(III)

wherein X is an integer between 5 and 7, inclusive. These compounds can be isolated from a liquid culture of Anarhinnum. A preferred method includes the steps of (a) contacting a liquid culture of Anarrhinum to a DNA methylation inhibitor; (b) after at least three days, contacting the culture, or a subculture thereof, with an elicitor; and (c) extracting the compound from the elicitor-contacted culture, or a subculture thereof The method can also include, between step (a) and step (b), the step of subculturing the culture. Preferably, the liquid culture is subcultured at least twice. Alternatively, these compounds can be made by the steps of (a) initiating a callus culture from an Anarrhinum seed; (b) culturing the initiated callus culture; (c) initiating a liquid culture from the callus culture; (d) contacting the liquid culture with a DNA methylation inhibitor; (e) subculturing the DNA methylation inhibitor-contacted liquid culture; (f) contacting the subculture with an elicitor; and (g) extracting the compound from the elicitor-contacted culture, or a subculture thereof Neither the DNA-methylation inhibitor step nor the elicitor step are required in order for the Anarrhinum liquid culture to yield the compounds of the invention, inclusion of these steps will augment their yield.

In another aspect, the invention features a substantially pure compound having the formula:

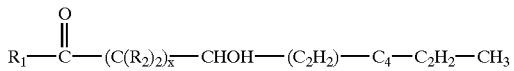

(IV)

wherein $R_1$ is a hydroxyl group or a moiety that can be replaced by a hydroxyl group in a hydrolysis reaction; each $R_2$ is independently H or a monovalent hydrocarbon moiety containing between 1 and 4 carbon atons, inclusive; and X is an integer between 3 and 9, inclusive. These compounds are useful in inhibiting the growth of fungal cells, e.g., for the treatment or prevention of fungal infections in plants and animals, including humans.

In another aspect, the invention features a substantially pure compound having the formula:

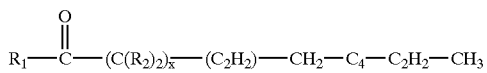

(V)

wherein $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atons, inclusive; and X is an integer between 3 and 9, inclusive. These compounds are useful in inhibiting the growth of fungal cells, e.g., for the treatment or prevention of fungal infections in plants and animals, including humans.

The compounds of the invention exhibit broad antifungal activity and high specific activity, and are thus useful for the treatment or prevention of fungal infections in both plants and animals, including living animals and plants, and plant products (e.g., grain or feed). Animals include mammals, particularly humans, as well as domestic animals bred for food or as pets, such as horses, cows, sheep, poultry, fish, pigs, cats, dogs, and zoo animals. Plants include trees, crops, grasses, and flowering plants.

Other features and advantages of the invention will be apparent from the following description of the preferred embodiments thereof and from the claims.

DETAILED DESCRIPTION

We have isolated novel antifungal compounds from plant cultures treated in sequence with a methylation inhibitor and an elicitor. These and related compounds, which can be made using standard organic synthesis techniques, are useful for the prevention or treatment of fungal infections.

Compounds

In the compounds of formula I:

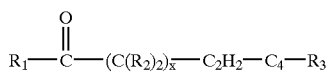

Figure 1:
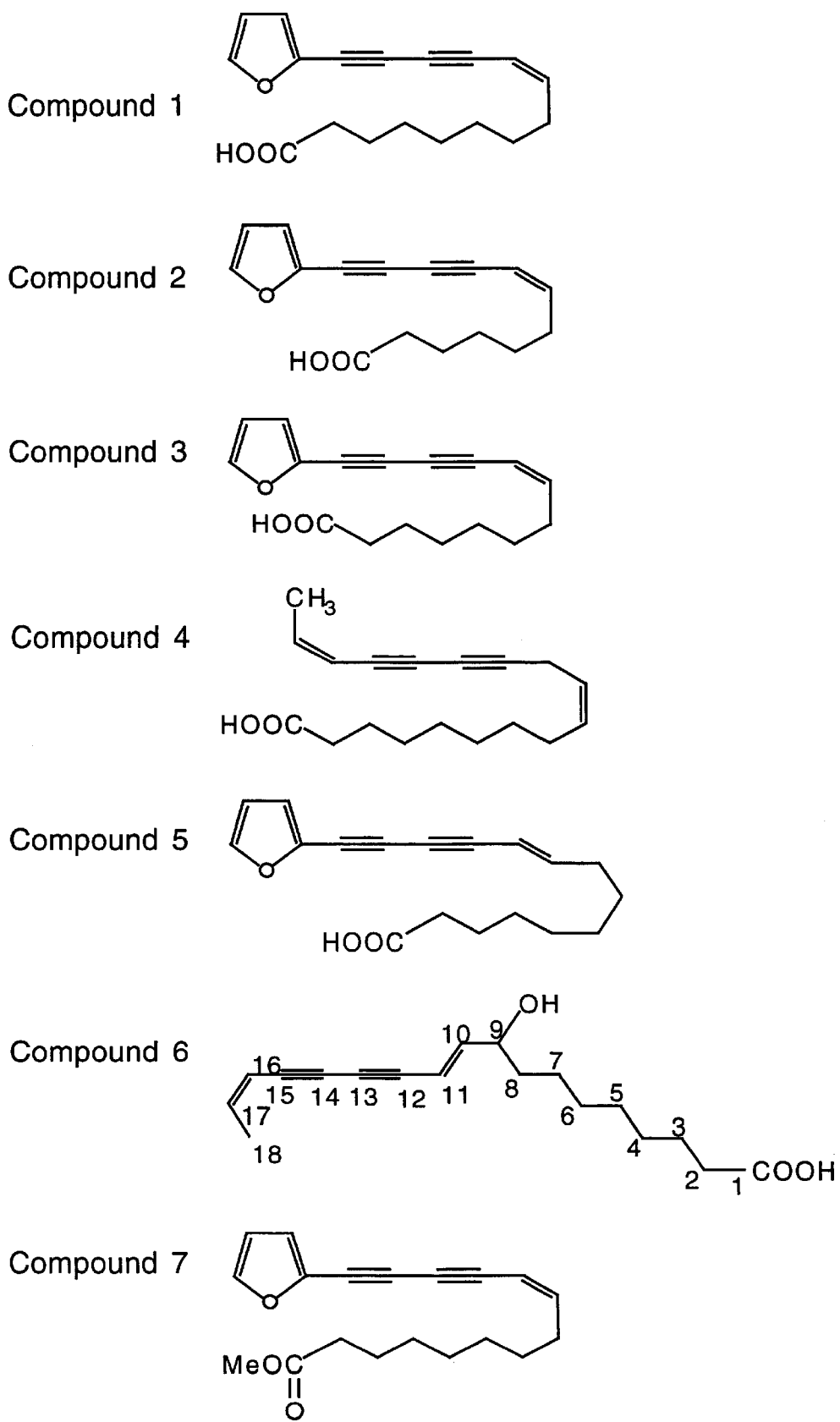
FIG. 1 is a schematic illustration showing the structure of Compounds 1–7.

(I)

the preferred $R_2$ moiety is H, as exemplified herein by compounds 1–7 (FIG. 1). Alternatively, one or more $R_2$ moieties can be replaced by hydrocarbon moieties such as methyl, ethyl, propyl, or butyl groups (or a combination thereof), without substantial loss of antifungal activity. Preferably, the sum of the carbons in the $R_2$ moieties is less than 15, more preferably less than 9, and most preferably less than 5.

In preferred compounds, such as compounds 1–3, 5, and 7, $R_3$ is a furan ring. Using standard methods of chemical synthesis, this ring can be replaced with a pyrrole or a thiophene ring; as the tertiary structure and charge distribution of the three rings are each similar, compounds having these latter rings will also likely have antifungal activity.

The variable X denotes the length of a saturated carbon backbone. The antifungal activity of the claimed compounds changes in part based on the length of this backbone. For example, Compounds 1, 5, and 7 (X=7) had the greatest anti-Candida activity, followed by Compound 3 (X=6), and then Compound 2 (X=5). Preferably, X is an integer between 5 and 7, inclusive, although longer carbon chains (X=8–10) may preserve or increase antifungal activity.

One preferred group of compounds have the formula:

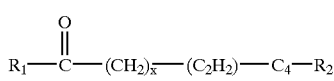

(II)

wherein $R_1$ is OH, $NH_3$, $OCH_3$, or $OC_2H_5$, $R_2$ is a pyrrole, furan, or thiophene ring, and X is an integer between 5 and 7, inclusive. Even more preferably, $R_1$ is OH, $R_2$ is a furan ring. Compounds within this formula (e.g., compounds 1–3, 5, and 7) have a hydrocarbon backbone that is unsubstituted.

The increased production of purified compounds of formulas III, IV, and V was induced in plant cell and tissue cultures following two treatments in sequence: treatment with a DNA methylation inhibitor and treatment with an elicitor. Treatment with a DNA methylation inhibitor is provided to an ungerminated seed, a germinating seed, an explant or tissue culture, or a liquid culture. Successive treatments with a DNA methylation inhibitor are also contemplated. For example, the invention encompasses a method including treating an ungerminated seed with a DNA methylation inhibitor (first treatment), germinating the treated seed, growing a callus from tissue derived from the germinated seed, inducing suspension from the callus, and treating a liquid suspension subculture with a DNA methylation inhibitor (second treatment). Whether a single treatment or successive treatments are used, ultimately, a liquid culture is derived from the DNA methylation inhibitor-treated plant cells or tissue.

DNA methylation inhibitor treatment affects the production of secondary metabolites by the treated plant cells. In part, the effect on treated plant cells is a temporary stress-induced effect. More importantly, the treatment also affects secondary metabolite production of subcultures derived from the treated ungerminated seed, germinating seed, explant or tissue culture, or liquid culture. The effect of DNA methylation inhibitor treatment is epigenetically stable with respect to altering the expression of secondary metabolism.

According to the methods of the invention, treatment with a DNA methylation inhibitor is generally combined with treatment of the derived liquid culture with an elicitor. Treatment with an elicitor also stimulates or promotes the production of secondary metabolites. Elicitation of a plant cell or tissue culture is generally performed when the plant liquid culture is established and can be grown to sufficient levels to enable the isolation of the compounds of the invention. Usually, the DNA methylation inhibitor-treated culture is subcultured (to remove residual DNA methylation inhibitor) prior to contact with the elicitor.

Methods of Synthesis of Compounds 1, 5, and 7

Figure 2:
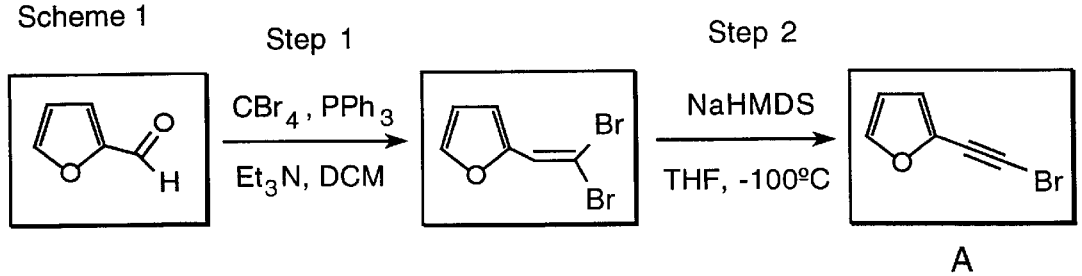
FIG. 2 is a schematic illustration showing a method of synthesis of Compounds 1, 5, and 7.
Figure 2:
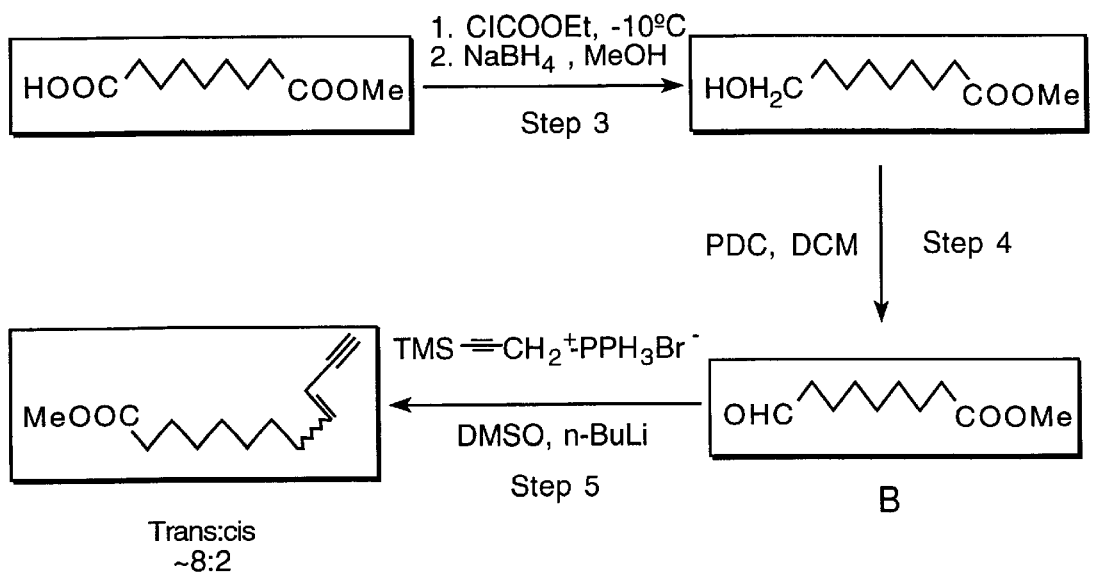
Figure 2:
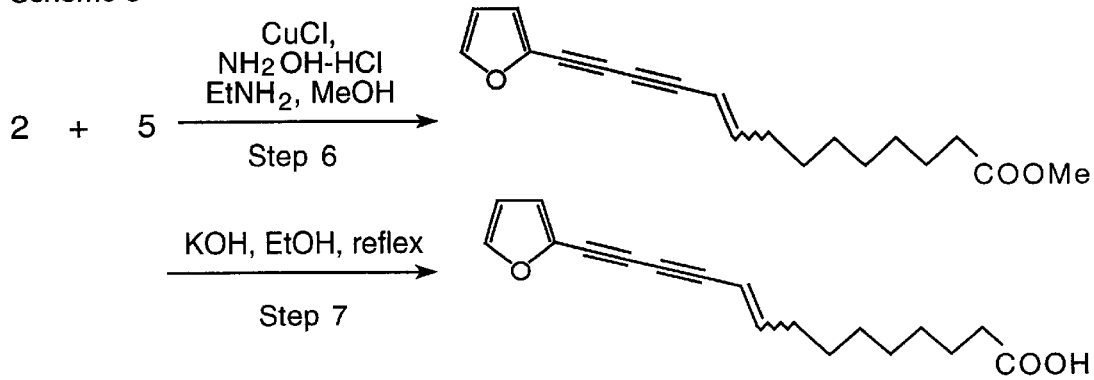

The compounds of the invention can be readily synthesized using standard methods of organic synthesis. An example synthesis of Compounds 1, 5, and 7 is provided below (FIG. 2).

Step 1: Synthesis of 2-(2,2-dibromo-vinyl)-furan

Carbon tetrabromide (20 mmole) was dissolved in anhydrous diohloromethane (200 mL), and kept at 20° C. under argon atmosphere. Triphenylphosphine (20 mmole) in dichloromethane (200 mL) was added dropwise. After 15 minutes of stirring, the reaction flask was kept at −60° C., followed by the addition of furaldehyde (10 mmole) and triethylamine (10 mmole) in dichloromethane (100 mL). The reaction mixture was brought to room temperature, and two volumes of ether were added. The precipitate was filtered, and the filtrate was dried. The crude material was purified by Si gel column chromatography (>50% yield).

Step 2: Synthesis of 2-bromoethynyl-furan 2-(2,2-Dibromo-vinyl)-furan (4 mmole) in tetrahydrofuran (40 mL) was maintained under argon atmosphere and cooled to −100° C. Sodium hexamethyl disilane (4.8 mmole, 1 M solution) in tetrahydrofuran was added dropwise to the reaction flask and stirred for 10 minutes. Saturated aqueous ammonium chloride solution was then added, and the reaction mixture was brought to the room temperature. Ether was used to extract the product from aqueous solution. Organic solvent was removed by rotavap, and the crude residue was used for next reaction in Step 6 (below).

Step 3: Synthesis of 9-hydroxy-nonanoic acid methyl ester

Azelaic acid monomethyl ester (20 mmole) was dissolved in tetrahydrofuran (100 mL) and kept in argon atmosphere at −10° C. Trietbylamine (30 mmole) was added dropwise to the reaction flask, followed by the addition of ethyl chloroformate (25 mmole). The solution was stirred for 20 minutes, and sodium borohydride (60 mmole) was added in one portion. Methanol (40 mL) was added dropwise and the reaction flask was kept at 0° C. for 40 minutes. Water (20 mL) was added and organic solvent was removed by rotavap. The residue was brought to water and ethyl acetate for partition. The organic layer was collected and dried to obtain 9-hydroxy-nonanoic acid methyl ester in decent purity for use in Step 4. The yield is >90%.

Step 4: Synthesis of 9-oxo-nonanoic acid methyl ester

9-Hydroxy-nonanoic acid methyl ester (7 g) in dichloromethane was treated with pyridinium dichromate (35 g) and stirred at room temperature for 12 hours. The pyridinium dichromate was filtered, and the organic filtrate was washed by water. Hexane (3× volume) was added to the solution, and organic layer was collected and dried to obtain the crude product. The product was purified by Si gel column chromatography to yield ~5 g of product.

Step 5: Synthesis of dodec-9-en-11-ynoic acid methyl ester n-Butyl lithium (750 μL, 2M) was added methyl sulfoxide (6 mL) under argon at room temperature. The solution was stirred for half an hour, and (3-trimethylsillyl-2-propynyl)-triphenylphosphonium bromide (1 mmole) in methyl sulfoxide was added and stirred for one hour. 9-Oxo-nonanoic acid methyl ester in methyl sulfoxide was added to the reaction mixture and stirred for 4.5 hours. The reaction mixture was poured onto ice water and extracted with ethyl acetate three times. The organic layers were combined and dried to obtain crude mixture, which was further purified through Si gel column chromatography. The product contained trans and cis isomers in about 8:2 ratio.

Step 6: Synthesis of methyl esters of Compound 1 and Compound 5

A methanol (100 μL) solution containing copper (I) chloride (0.6 mg), hydroxylamine hydrochloride (3 mg), and ethylamine (70% in water, ~100 μL) was added to dodec-9-en-11-ynoic acid methyl ester (~3.2 mg) in methanol, followed by the addition of 2-bromoethynyl-furan (~2 mg) in methanol. The reaction mixture was kept at 0° C. for 20 minutes and water and ether was added. The organic layer was collected and dried. A mixture of methyl esters of Compounds 1 and 5 (~1 mg) was obtained by Si Gel preparative thin layer chromatography (PTLC) in a trans-cis ratio of 8:2. One of these methyl esters is Compound 7.

Step 7: Synthesis of Compound 1 and Compound 5

The mixture of methyl esters of Compound 1 and Compound 5 (4.7 mg) of Step 6 was dissolved in ethanol-water and added with 2N potassium hydroxide (400 μL). The solution was refluxed for one hour and cooled to room temperature. Hydrochloride solution (800 μL; 1N) was added and the solution was extracted with ethyl acetate. A total of 4 mg of Compounds 1 and 5 (trans:cis ratio of ~8:2) was obtained after removal of organic solvent.

One skilled in the art will recognize that other compounds of the invention can be made using variations of the foregoing method, or by using other standard methods of organic synthesis. Such methods are described, for example, in van Hijfte et al., Tetrahedron lett. 30: 3655; Hauske et al., Tetrahedron Lett. 33: 3715, 1992; and Grandjean et al., Tetrahedron Lett. 35:3529–3530, 1994, each of which is hereby incorporated by reference.

Pharmaceutical Therapeutics and Plant Protectants

The invention features compounds capable of inhibiting the growth, pathogenicity, or virulence of a pathogen. Accordingly, these compounds have medicinal or agricultural value as drugs or plant protectants. Examples of pathogenic fungi that can be inhibited by the compounds of the invention are, for example, *C. albicans,* Aspergillus spp., Mucor spp., Rhizopus spp., Fusarium spp., *Penicillium marneffei,* Microsporum spp., *Cryptococcis neoformans, Pneumocystis carinii,* and Trichophyton spp.

The invention features pharmaceutical compositions that include one or more compounds of the invention. For therapeutic uses, the compositions or compounds may be administered systemically, for example, formulated in a pharmaceutically-acceptable buffer such as physiological saline. Treatment may be accomplished directly, e.g., by treating the animal with a compound or composition of the invention. Preferable routes of administration include, for example, inhalation or subcutaneous, intravenous, interperitoneally, intramuscular, or intradermal injections which provide continuous, sustained levels of the drug in the patient. Treatment of human patients or other animals is carried out using a therapeutically effective amount of a compound of the invention in a physiologically-acceptable carrier. Suitable carriers and their formulation are described, for example, in *Remington: The Science and Practice of Pharmacy*, (19th ed.) ed. A. R. Gennaro A R., 1995, Mack Publishing Company, Easton, Pa. The amount of the antifungal agent to be administered varies depending upon the manner of administration, the age and body weight of the patient, and the type of disease and extensiveness of the disease. Generally, amounts will be in the range of those used for other agents used in the treatment of fungal diseases. A compound is administered at a dosage that inhibits fungal growth or survival. For example, for systemic administration a compound is administered typically in the range of 0.1 ng to 10 g/kg body weight.

In one preferred method, one or more compounds of the invention are formulated in combination with a solid or a liquid dermatologically acceptable carrier. Useful solid carriers include finely divided solids such as talc, clay, microcrystalline cellulose, silica, alumina, and the like. Useful liquid carriers include water, alcohols, or glycols (or water-alcohol/glycol blends), in which the present compounds can be dissolved or dispersed at effective levels. Adjuvants (such as flavorings fragrances), surfactants, and additional antimicrobial agents. can be added to optimize the properties for a given use. The compositions can be applied from absorbent pads, used to impregnate bandages and other dressings, or sprayed onto the affected area using pump-type or aerosol sprayers. The liquid compositions can also be employed as eyedrops, mouth washes, douches, etc.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

The total concentration of one or more compounds of the invention in the present compositions can be varied widely, and will depend on factors such as the compatibility of the active ingredient(s) with the vehicle, the potency of the active ingredient(s) and the condition to be treated. Generally, the concentration of the compound(s) of formula in a liquid composition, such as a lotion, will be from about 0.1–25% by weight, preferably from about 0.5–10% by weight, and more preferably from about 0.5% to 5% by weight. The concentration in a semi-solid or solid composition such as a gel or a powder will be about 0.1–5% by weight, and preferably about 0.5–2.5% by weight.

For agricultural uses, the compositions or agents disclosed herein may be used, for example, as chemicals applied as sprays or dusts on the foliage of plants, or in irrigation systems. Typically, such agents are administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of fungal pathogens. Treatment is preferably done several days or weeks before planting. The chemicals can be applied by either a mechanized route, e.g., a tractor, or with hand applications. In addition, compounds of the invention can be used as disinfectants.

In other medical applications, an antifungal compound can be added to materials used to make medical devices such as catheters, including but not limited to intravenous, urinary, intraperitoneal, ventricular, spinal, and surgical drainage catheters, in order to prevent colonization and systemic seeding by potential fungal pathogens. Similarly, an antifungal compound may be added to the materials that constitute various surgical prostheses and to dentures to prevent colonization by fungal pathogens and thereby prevent more serious invasive infection or systemic seeding by these pathogens.

Assays for Antifungal Activity

The ability of an agent to inhibit fungal growth and, thus, the course of infection by a pathogenic organism can be demonstrated by an in vitro experiment measuring growth of that organism, or by using an enzyme- or cell-based inhibition assay as an indirect marker of growth. Inhibition is preferably described by an $IC_{50}$ (concentration of a compound required for 50% inhibition) or as a MIC (the minimal inhibitory concentration, i.e., the lowest concentration of the compound that inhibits the growth of the organism). Thus, a lower $IC_{50}$ or MIC indicates that a compound has greater growth-inhibiting activity. A compound with increased specificity demonstrates one or more of the following: preferential inhibition of a microbial enzyme over a corresponding or similar enzyme in the host cell or tissue; preferential inhibition of one microbial enzyme over another microbial enzyme; and preferential inhibition of the growth of a microbe over the growth of the host cell or tissue. In general, an active compound preferably inhibits growth, measured by a given parameter, by at least 25% (e.g., at least 30%, at least 40%, at least 50%, or at least 65%) when compared to an organism not contacted with the compound.

Specific examples of pharmacological assays include those which measure inhibition of the following: *C. albicans* (e.g., ATCC #90028) growth, fungal-specific chitin synthase, or glucan synthase. Additional assays measure the efficacy of the agent in prolonging the life of mice infected with a lethal challenge of either fluconazole-sensitive or fluconazole-resistant *C. albicans* (see, for example, Lo et al., Cell 90:939–949, 1997).

A preferred compound is broadly effective against one or more Candida spp., such as *C. albicans, C. krusei, C. glabrata, C. tropicalis, C. parapsilosis, C. guilliermorulii, C. haemulonii, C. lusitaniae, C. norvegensis, C. viswanathii,* and *C. kefyr,* as well as others discussed herein. A preferred compound is also effective against fungal infections such as *Aspergillus fumigatus, A. flavus, A. niger, Histoplasma capsulatum* (var. *capsulatum*), *Coccidioides immitis, Cryptococcus neoformans* (var. *neoformans,* and var. *gattii*), *C. bidus, C. laurentii,* and *C. fusarium,* as well as Mucormycotic organisms such as *Rhizopus oryzae, R. micropsorus, R. pusillus, Cunninghamelle bertholletiae, Saksenaea vasiformis, Mucro circinelloides, M. ramosissimus, Absidia corymbifera, Apophysomyces elegans, Cokeromyces recurvatus,* and *Syncephalastrum racemosum.* Disclosed compounds may demonstrate activity against more than one type of organism and are therefore particularly suitable and effective for administration to patients with more than one type of infection (e.g., a patient may have two types of fungal infections). Certain disclosed compounds may also demonstrate additivity or synergy when administered in combination with other therapeutics such as azoles (e.g., fluconazole) and amphotericin B. Preferably, compounds are screened for mammalian cell toxicity (e.g., in Vero (monkey kidney) or U937 (human monocytic) cell lines); compounds with low mammalian cell toxicity at a concentration that inhibits fungal growth are particularly preferred.

Inhibition of Candida spp. Growth

There are numerous assays that can be used to measure the inhibition of growth of a fungus such as Candida. In one example, cultures of Candida, e.g., *C. albicans* strains DSY1024 and SC5314, *C. krusei* ATCC 6258, and *C. glabrata* ATCC 90030, are subcultured from cryopreserved stocks onto Sabouraud's dextrose agar plates. Blastoconidia are suspended into RPMI-MOPS medium and inoculated (500 cfu/well) into 96-well plates containing test compounds in a final volume of 100 µL/well. After 22 hours at 35° C., 25 µL of XTT (2,3-bis(2-methoxy-4-nitro-5-sulfophenyl)-5-(phenylamino)carbonyl]-2H-tetrazolium hydroxide), (100 µg/mL) with PMS (phenazine methyl sulfate, 5 µM) are added to each well, followed by 2 hours of shaking. Growth is assessed spectrophotometrically by measuring the appearance of soluble formazan stain at 450 nm using an $E_{max}$ microplate reader. Validity of the assay is confirmed by determination of the *C. albicans* minimum inhibitory concentration (MIC) for known antifungal agents such as amphotericin B, 5-flucytosine, fluconazole, nikkomycin Z, and polyoxin D.

Those in the art will recognize that any assay that measures growth of any fungus can readily be adapted to determine the inhibition of fungal growth by compounds of the present invention.

Inhibition of Fluconazole-Resistant and Fluconazole-Sensitive Candidiasis in Mice Immunocompetent mice (ICR, Sprague-Dawley, Indianapolis, Ind.) are infected with a pathogenic strain (e.g., strain #64) of *C. albicans* that is sensitive to fluconazole. After 24 hours, dissemination of infection has been shown by organ colony counts (kidney, spleen, and liver) greater than $10^5$ colony forming units (CFU). Treatment is begun 24 hours after infection with dosage once a day for 10 days. Untreated control mice usually die after about 16 days. After 30 days the percent survival in the group treated with fluconazole (40 mg per kg body weight, twice a day) is about 30%. In addition to measuring animal viability, the organ fungal load (in CFU) can measured.

In a similar experiment using a fluconazole-resistant clinical isolate (e.g., *C. albicans* UTR-14), the percent survival after 20 days of the group treated with fluconazole (40 mg per kg body weight p.o. (twice daily)) and in the untreated group is each usually 0%.

Inhibition of *C. albicans* with Drug Combinations

The compounds of the invention may be tested in combination with known antifungal agents (e.g., amphotericin B and fluconazole) using any of the foregoing assays. Compounds that, in combination with known antifungal agents, are particularly useful compounds, as they may be incorporated into a regiment for treating or preventing fungal infection.

The following examples are to illustrate the invention. They are not meant to limit the invention in any way.

EXAMPLE 1

Isolation of Antifungal Compounds from *Anarrhinum bellidifolium*

A plant cell culture of *A. bellidifolium* (Scrophulariaceae) was prepared using seeds of *A. bellidifolium*. The seeds were sterilized by 15 minutes immersion in 5% Domestos (active chlorine 0.25%). Sterile seed were placed on seed germination media (B83 modified after Gamborgs B5 recipe), +sucrose (1%), no hormones, and B83+propiconazole (10 mg/L)). Upon germination and appropriate growth of roots/shoots, the sterile seedlings were chopped into small pieces of approximately 5 mm and placed upon solidified callus induction medium B50 (modified after Gamborgs B5 recipe to contain 2,4-dichlorophenoxyacetic acid (2,4-D) (1 mg/L), kinetin (0.1 mg/L), coconut water (100 ml/L), sucrose (2%)). Upon production of callus the material was used to initiate suspension cultures.

To establish suspension cultures, portions of seedling explant+callus were placed in B88, modified after Gamborgs B5 recipe (Gamborg et al., Exp. Cell. Res. 50:151–158, 1968) to contain 2,4-D (1 mg/L), kinetin (0.1 mg/L), coconut water (100 ml/L)+3% sucrose. The suspension media were replenished at 14 day intervals. After 3 months, the established liquid suspension culture was routinely maintained in a 250 mL conical flask, by transferring 28 mL of 14 day old suspension culture into 100 mL fresh B88 medium. The culture was incubated at 25° C. in continuous dark and shaken at 140 rpm.

A 2 L conical flask containing 750 mL of production medium B49 (Garmborgs B5, 5% sucrose, no hormones) was inoculated with 256 mL of 14 day old suspension culture. After 7 days' growth, filter-sterilized methyl jasmonate (250 uM final concentration) and an autoclaved *Candida albicans* preparation (50 mg/L final concentration) were added. The cell cultures were harvested by vacuum filtration after a further 6 days. The *C. albicans* preparation was obtained by growing a culture of ATCC 28516 on YEPD media (yeast extract 1%, yeast peptone 2%, glucose 2%) to maximum cell density and twice autoclaving the total yeast culture prior to addition to plant cultures.

Subsequent re-growths were made using material which had undergone several rounds of short term cold storage whereby 140 mL of 3-day old culture were placed in a flat 600 mL tissue culture flask with vented lid and then stored at 15° C. for 91 days. The culture was then removed and placed in a 250 mL conical flask with media being replaced at 14 day intervals until the culture could be routinely maintained by transferring 40 mL of 14 day culture into 100 mL fresh B88 medium. After harvesting, the separated cells were freeze-dried before extraction.

EXAMPLE 2

Isolation of Compounds 1–5

The freeze-dried cell biomass (41 g) from 6 liters cell culture AB-03499-T2 (*A. bellidifolium*) was thawed and washed well with water, then dried. This was extracted with 2 liters of methylene chloride/methanol 1:1. The dried extract (2.8 g) was absorbed and fractionated on a Diaion HP-20® column (i.d 2.5 cm, 25 cm deep) and eluted with $H_2O$, 20% MeOH in $H_2O$, MeOH and acetone to afford fractions A1, A2, A3 and A4, respectively. HPLC analysis showed that most acetylene derivatives were found in fraction A3 (Nova-pak HR C-18 column (3.9×300 mm), gradient from 20% $CH_3CN$ (0.1% HCOOH) to 100% $CH_3CN$. (0.1% HCOOH) in 14 minutes). Fraction A3 (310 mg) was subfractioned by gravity column chromatography (reverse phase C-18) using as solvent system 40% MeOH to afford Compound 1 (50 mg) Compound 2 (6 mg), Compound 3 (5 mg), and a complex mixture (7 mg) that was further purified over normal phase silica gel column chromatography using a mixture of hexanes and acetone (5:1) to yield Compound 4 (3 mg) and Compound 5 (2 mg).

Compound 1. UV: 247, 260, 289, 308, 328; Molecular Formula: $C_{18}H_{20}O_3$. ESMS: m/z 283 [M−H]⁻ in negative mode, m/z 307 [M+Na]⁺ in positive mode, in Hewlett Packard; HRFABMS: m/z 284.1419 (cald. 284.1412) [M]+, m/z 307.1297 (calcd. 307.1311) [M+Na]+, in Finnigan MAT95Q, at m/Δm=4,000 using the 10 percent valley definition. The matrix was 3-nitrobenzyl alcohol. NMR data: see Table 1. for proton on a Varian Unity instrument).

Compound 2. ESMS m/z: 279 [M+Na]+ (Calcd for $C_{16}H_{16}O_3Na$ [279].

Compound 3. Amorphous gum: UV (MeOH$_{max}$ nm: 213, 247, 260, 290, 308, and 328; $^1H$- and $^{13}C$-NMR: Table 1; ESMS m/z: 293 [M+Na]+ (calcd for $C_{17}H_{18}O_3Na$ [293]).

Compound 4. Amorphous gum: UV (MeOH$_{max}$ nm: 213, 247, 260, 290, 308, and 328; $^1H$- and $^{13}C$-NMR: Table 1; ESMS m/z: 295 [M+Na]+; (calcd for $C_{18}H_{20}O_2Na$ [295]).

Compound 5. Amorphous gum: UV (MeOH$_{max}$ nm: 213, 247, 260, 290, 308, and 328; $^1H$- and $^{13}C$-NMR: Table 1; ESMS m/z: 307 [M+Na]+(calcd for $C_{18}H_{20}O_3Na$ [307]).

TABLE 1

| | Compound 1 | | Compound 2 | | Compound 3 | | Compound 4 | | Compound 5 | | Compound 6 | | Compound 7 | |
|---|---|---|---|---|---|---|---|---|---|---|---|---|---|---|
| | δ C | δ H | δ C | δ H | δ C | δ H | δ C | δ H | δ C | δ H | δ C | δ H | δ C | δ H |
| 1 | 177.7(s) | 2.28(t, J=7.5 Hz, 2H) | 177.6 (s) | | 177.7 (s) | 2.30(t, J=7.5 Hz) | 177.8 (s) | | 177.9 (s) | | 177.8 (s) | | 176.0 (s) | |
| 2 | 34.9(t) | 1.60 (m, 2H) | 34.8(t) | 2.31(t, J=7.5 Hz) | 34.9(t) | 1.62(m) | 35.0 (t) | 2.28(t, J=7.5 Hz) | 35.0 (t) | 2.28 (t, J=7.5 Hz) | 35.1 (t) | 2.28 (t, J=7.2 Hz, 2H) | 34.8 (t) | 2.33 (t, J=7.5 Hz, 2H) |
| 3 | 26.1(t) | 1.36(m) | 25.9(t) | 1.63 (m) | 26.0(t) | 1.50–1.29 (m)$^b$ | 26.1 (t) | 1.60(m) | 26.1 (t) | 1.60(m) | 26.1 (t)$^a$ | 1.60(m, 2H) | 26.0 (t) | 1.63(m) |
| 4 | 30.1(t)$^a$ | 1.36(m) | 29.7 (t)$^a$ | 1.51–1.29 (m)$^c$ | 29.8 (t)$^a$ | 1.51–1.29(m)$^b$ | 30.1 (t)$^a$ | 1.41–1.30 (m)$^c$ | 30.1 (t)$^a$ | 1.50–1.29 (m)$^b$ | 30.1 (t)$^a$ | 1.36(m) | 30.1 (t) | 1.36(m) |
| 5 | 30.1(t)$^a$ | 1.36(m) | 29.5 (t)$^a$ | 1.51–1.29 (m)$^c$ | 30.0 (t)$^a$ | 1.51–1.29(m)$^b$ | 30.3 (t)$^a$ | 1.41–1.30 (m)$^c$ | 30.1 (t)$^a$ | 1.51–1.29 (m)$^b$ | 30.2 (t)$^a$ | 1.36(m) | 30.0 (t)$^a$ | 1.36(m) |
| 6 | 30.0(t)$^a$ | 1.36(m) | 31.7(t) | 2.38(q, J=7.5 Hz) | 29.7 (t)$^a$ | 1.50–1.29(m)$^b$ | 30.3 (t)$^a$ | 1.41–1.30 (m)$^c$ | 30.0 (t)$^a$ | 1.50–1.29 (m)$^b$ | 30.4 (t)$^a$ | 1.36(m) | 29.9 (t)$^a$ | 1.36(m) |
| 7 | 29.6(t) | 1.46(m, 2H) | 150.1 (d) | 6.22 (dt, J=10.8, 7.5 Hz) | 31.7(t) | 2.38 (q,J=7.5 Hz) | 30.2 (t)$^a$ | 1.41–1.30 (m)$^c$ | 29.5 (t)$^a$ | 1.50–1.29 (m)$^b$ | 26.2 (t)$^a$ | 1.37(m) | 29.6 (t) | 1.47(m) |
| 8 | 31.7(t) | 2.36(qd, J=7.5, 1.2 Hz, 2H) | 108.7 (d) | 5.64 (br d, J=10.8 Hz) | 150.3 (d) | 6.22(dt, J=10.8, 7.5 Hz) | 28.0 (t) | 2.09(q,d J=6.6, 1.2 Hz) | 31.7 (t) | 2.19(qd, J=7.5, 1.2 Hz) | 33.5 (t) | 1.49(m) | 31.7 (t) | 2.37(qd, J=7.5, 1.2 Hz, 2H) |
| 9 | 150.4 (d) | 6.21(dt, J=10.8, 7.5 Hz, 1H) | 82.3(s) | | 108.7 (d) | 5.64 (dt, J=10.8, 1.2 Hz) | 133.7 (d) | 5.55–5.48 (m)$^d$ | 151.1 (d) | 6.40(dt, J=15.9, 1.2 Hz) | 86.4 (d) | 4.30 (q, J=7.2 Hz, 1H) | 150.4 (d) | 6.22(dt, J=10.8, 7.5 Hz, 1H) |
| 10 | 108.6 (d) | 5.63(dt, J=10.8, 1.2 Hz, 1H) | 78.9(s) | | 82.4(s) | | 123.7 (d) | 5.64(dtt, J=10.8, 6.6, 1.2 Hz) | 109.2 (d) | 5.67(dt, J=15.9, 1.2 Hz) | 147.7 (d) | 6.23(dd, J=15.9, 7.2 Hz, 1H) | 108.6 (d) | 5.65(dt, J=10.8, 1.2 Hz, 1H) |
| 11 | 82.4(s) | | 77.6(s) | | 78.9(s) | | 18.4 (t) | 3.10(d, J=6.6 Hz) | 84.4 (s) | | 112.0 (d) | 5.85(d, J=15.9, 7.2 Hz, 1H) | 82.4 (s) | |
| 12 | 79.0(s)$^b$ | | 71.9(s) | | 77.6(s) | | 83.5 (s) | | 79.2 (s) | | 80.9 (s)$^b$ | | 79.0 (s)$^b$ | |
| 13 | 77.6(s)$^b$ | | 137.8 (s) | | 71.9(s) | | 65.6 (s) | | 77.4 (s) | | 75.0 (s)$^b$ | | 77.6 (s)$^b$ | |
| 14 | 71.9(s) | | 119.0 (d) | 6.80 (d, J=3.3 Hz) | 137.7 (s) | | 72.7 (s) | | 70.5 (s) | | 78.9 (s)$^b$ | | 71.9 (s) | |
| 15 | 137.7(s) | | 112.3 (d) | 6.49 (dd, J=3.3, 1.8 Hz) | 119.0 (d) | 6.80 (dd, J=3.3, 0.6 Hz) | 79.5 (s) | | 137.7 (s) | | 79.1 (s)$^b$ | | 137.7 (s) | |
| 16 | 119.0 (d) | 6.78(dd, J=3.3, 0.9 Hz, 1H) | 146.3 (d) | 7.55(d, J=1.8 Hz) | 112.3 (d) | 6.49(dd, J=3.3, 1.8 Hz) | 110.0 (d) | 5.55–5.48 (m)$^d$ | 118.8 (d) | 6.77(br d, J=3.3 Hz) | 109.9 (d) | 5.59(bd, J=10.8 Hz) | 119.0 (d) | 6.80(dd J=3.3, 0.9 Hz, 1H) |
| 17 | 112.3 (d) | 6.47(dd, J=3.3, 1.8 Hz, 1H) | | | 146.3 (d) | 7.55(d, J=1.8 Hz 0.6 Hz) | 143.0 (d) | 6.15(dq, J=10.8 6.9 Hz) | 112.2 (d) | 6.47 (dd, J=3.3, 1.8 Hz) | 143.8 (d) | 6.20(dq, J=10.8, 6.89 Hz, 1H) | 112.3 (d) | 6.49(dd, J=3.3, 2.1 Hz, 1H) |

TABLE 1-continued

| | Compound 1 | | Compound 2 | | Compound 3 | | Compound 4 | | Compound 5 | | Compound 6 | | Compound 7 | |
|---|---|---|---|---|---|---|---|---|---|---|---|---|---|---|
| | δ C | δ H | δ C | δ H | δ C | δ H | δ C | δ H | δ C | δ H | δ C | δ H | δ C | δ H |
| 18 | 146.3 (d) | 7.53(dd, J=1.8, 0.9 Hz, 1H) | | | | | 16.3 (q) | 1.88(dd, J=6.9, 1.8 Hz) | 146.2 (d) | 7.53(br d, J=1.8 Hz) | 16.4 (q) | 1.90(dd, J=6.9, 1.8 Hz, 3H) | 146.3 (d) | 7.55(dd, J=2.1, 0.9 Hz, 1H) |

EXAMPLE 3
Isolation of Antifungal Compounds from *Anarrhinum corsicum*

A plant cell culture of *A. corsicum* (Scrophulariaceae) was prepared using seeds of *A. corsicum*. The seeds were sterilized by 30 minutes immersion in 30% Klorin+Tween 20 followed by 3% $H_2O_2$ for 3 minutes. Sterile seeds were placed on seed germination media (B83 modified after Gamborgs B5 recipe, +sucrose (1%), no hormones, and B83+propiconazole (10 mg/L)). Upon germination and appropriate growth of roots/shoots, the sterile seedlings were chopped into small pieces of approximately 5 mm and placed upon solidified callus induction medium B50 (modified after Gamborgs B5 recipe to contain 2,4-D (1 mg/L), kinetin (0.1 mg/L), coconut water (100 ml/L), sucrose (2%)). Callus was established two months after initiation.

To establish suspension cultures, portions of established callus were placed in B105, modified after Gamborgs B5 recipe to contain 2,4-D (1 mg/L), kinetin (0.1 mg/L), coconut water (100 ml/L), glutamine (1.46 mg/L)+3% sucrose. The suspension media were replenished at 14 day intervals. After 2 months, the established suspension culture was routinely maintained in a 250 mL conical flask, by transferring 40 mL of 14 day old suspension culture into 100 mL fresh B105 medium. The culture was incubated at 25° C. in continuous dark and shaken at 140 rpm.

The culture was prepared for sample production as follows: A 40 mL aliquot of the suspension was taken at Day 0, and transferred to a 100 mL flask. On day three, a sterile solution of 5-azacytidine (5-AC) in water was added to a final concentration of $3 \times 10^{-5}$ M, and the resultant mixture was incubated for 11 days. The 40 mL 5-AC-treated culture was then subcultured twice before being transferred to larger scale for further manipulation.

A 500 mL conical flask containing 190 mL of production medium B49 (Gamborgs B5, 5% sucrose, no hormones) was inoculated with 70 mL of 14 day old suspension culture. After 7 days growth, filter-sterilized methyl jasmonate (250 μM final concentration) and an autoclaved C. albicans preparation (50 mg/L final concentration) were added. The cell cultures were harvested by vacuum filtration after a further 6 days. The *C. albicans* preparation was obtained by growing a culture of ATCC28516 on YEPD media (yeast extract 1%, yeast peptone 2%, glucose 2%) to maximum cell density and twice autoclaving the total yeast culture prior to addition to plant cultures.

After harvesting, the separated cells were freeze-dried before extraction.

EXAMPLE 4
Isolation of Compound 6

LP416E8 (AC-05081-T4-3) was an organic extract of a manipulated plant cell culture from *A. corsicum*. This extract was the subject of bioactivity directed fractionation because it exhibited antifungal activity in a screen against the multidrug resistant (MDR) quadruple knock-out strain *C. albicans* DSY1024. The $IC_{50}$ of the original extract for LP416E8 was 3.2 μg/mL against this organism.

The crude cell biomass from a 20 liter culture was filtered and washed with distilled water. The dried biomass (393 g) was mixed with 2 liters of dichloromethane and methanol (1:1), and stirred for 1.5 hours. The biomass was removed by filtration. The extraction procedure was repeated three times. The dried organic extract (19.7 g) was obtained by removing solvent under vacuum in a rotary evaporator.

The dried extract (19.0 g) was mixed with HP-20® polystyrene resin, and then applied to a HP-20® polystyrene resin column (2000 mL), which has been equilibrated with 100% distilled water. The column was eluted with a step gradient solvent system with 2 liter fractions of increasing concentrations of acetonitrile in water (25%, 40%, 60%, 70%, 80%). The column was then eluted sequentially with 2 liter portions of methanol, acetone, and dichloromethane. Solvent was removed from each fraction under vacuum. The fractions, with weights given in parentheses, were designated in order of elution, A1 (9.33 g), A2 (1.55 g), A3 (0.40 g), A4 (0.49 g), A5 (0.32 g), A6 (0.60 g), A7 (2.38 g), an A8 (0.67 g). The active fraction A6 (0.60 g) was further fractionated by Sephadex LH-20® column chromatography, eluted with hexane-dichloromethane (1:1) and then washed with methanol to give fractions; B1 (8 mg), B2 (78 mg), B3 (104 mg), B4 (12 mg), B5 (4 mg), B6 (26 mg), and B7 (0.7 mg). Fraction B4 was identified as Compound 1. Fraction B3 was passed through another Sephadex LH-20® column eluted with the same solvent system and 26 fractions were collected. The fractions C22, C23, and C24 were combined to yield a total of 13 mg identical to Compound 1 by TLC and $^1$HNMR.

Fractions C6 to C9 were further fractionated to obtain Compound 4 and Compound 6. Each was first applied to silica gel preparative TLC plates. The plates were developed with n-hexane-EtOAc (3:1) twice. The highest Rf band, as visualized by irradiation with UV light, from each plate (fractions C6D1, C7D1, C8D1, and C9D1) were removed and extracted with acetone. Four organic extracts were combined and concentrated. to yield Compound 5 (~4 mg), identified by NMR and MS data (Table 1).

The third highest Rf bands of the preparative TLC plates above for fractions C8 and C9 were removed and extracted with acetone. The two organic extracts were combined to yield Compound 6 (~3 mg) identified by NMR and MS data (Table 1).

EXAMPLE 5
Methylation of Compound 1

3.3 mg of Compound 1 was dissolved in 1 mL MeOH, and excess trimethylsilyl-diazomethane (~0.3 mL) was added to the solution. The reaction mixture was kept unstirred for 5 hours at room temperature. The solvent and excess reagent was removed with a stream of nitrogen. The residue was dissolved in hexane and applied to a silica gel PTLC, developed with hexane-EtOAc (3:1). The major band with Rf ~0.9 was removed and extracted with acetone. The acetone was removed with a stream of nitrogen, and 2.5 mg of Compound 7 (the methyl ester of Compound 1) was obtained (Table 1).

EXAMPLE 6
Inhibition of Fungal Growth by Compound 1

Using the cell growth assay described herein, Compound 1 was tested for its ability to inhibit growth of *C. albicans, C. kefyr, C. tropicalis, C. krusei,* and *C. glabrata.* The MIC and $IC_{50}$ values are presented in Table 2. The growth of all tested strains, including that of *C. albicans* strains 93-1226 and UTR-14, which are fluconazole-resistant, was inhibited at $IC_{50}$ values of 0.35 to 42 ng/mL.

TABLE 2

|  | MIC (ng/mL) | $IC_{50}$ (ng/mL) |
|---|---|---|
| *C. albicans* | | |
| DSY1024 | 0.625 | 0.35 |
|  | 1.25 | 1.2 |
|  | 2.5 | 1.6 |
| SC5314 | 0.625 | .36 |
|  | 1.25 | 1.2 |
|  | 2.5 | 1.5 |
| 90028 | 1.25 | 1.22 |
| A26 | 1.25 | 1.10 |
| #64 | 5 | 1.45 |
| UTR-14[a] | 2.5 | 3.64 |
| 93-1226[a] | 2.5 | 2.10 |
| *C. keyfer* | | |
| 46764 | 10 | 10-5 |
| *C. tropicalis* | | |
| 623-20 | 5 | 2.96 |
| 750 | 5 | 4.67 |
| 97-1037 | 5 | 3.68 |
| *C. krusei* | | |
| 6258 | 50 | 41.90 |
| 97-1037 | 50 | 26.10 |
| *C. glabrata* | | |
| 90030 | 5 | 12.5–25 |
| 95-2421 | 12.5 | 8.25 |
| 95-2425 | 12.5 | 3.13–6.25 |

[a]Fluconazole-resistant strain

The anti-cell growth activity of Compound 1 on other fungal strains, as well as bacterial strains and cultured mammalian cells, was also tested (Table 3). Fungal growth was inhibited with $IC_{50}$ values in the range of 180 ng/mL to 100 mg/mL. Bacterial cell growth and mammalian cell growth was inhibited at substantially higher concentrations of Compound 1.

TABLE 3

|  | MIC (µg/ml) | $IC_{50}$ (µg/ml) |
|---|---|---|
| *S. cerevisiae* AD1-9 | 0.25 | 0.18 |
| *S. cerevisiae* 2229-5C | 1 | 0.5–1.0 |
| *A. fumigatus* 8001 | 200 | 50–100 |
| *S. aureus* 29213 | 50 | 31.6 |
| *E. faecalis* 29212 | 12.5 | 7.5 |
| *E. coli* 700 | >200 | na |
| Vero cells | na | 31.0, 5.7 |
| HFF cells | na | 12 |

EXAMPLE 7
Inhibition of Fungal Growth by Compounds 2–7

Using the general cell growth assay described herein, Compounds 2–7 were assayed for their ability to inhibit the growth of *C. albicans* strains DSY1024 and SC5314. The results are presented in Table 4. Each of the compounds inhibited growth of strain DSY1024, which has four MDR mutations, and thus is expected to be more sensitive to growth inhibitors. Compounds 2, 6, and 7 were also able to inhibit growth of strain SC5314.

TABLE 4

|  |  | DSY1024 | SC5314 |
|---|---|---|---|
| Compound 2 | MIC (ng/ml) | 3125 | 3125 |
|  | $IC_{50}$ (ng/ml) | 1817 | 2592 |
| Compound 3 | MIC (ng/ml) | 1000 | nt |
|  | $IC_{50}$ (ng/ml) | 503 | nt |
| Compound 4 | MIC (ng/ml) | 100000 | 100000 |
|  | $IC_{50}$ (ng/ml) | 68000 | 88200 |
| Compound 5 | MIC (ng/ml) | 7.8 | nt |
|  | $IC_{50}$ (ng/ml) | 3.9 | nt |
| Compound 6 | MIC (ng/ml) | 12500 | 12500 |
|  | $IC_{50}$ (ng/ml) | 11300 | 8500 |
| Compound 7 | MIC (ng/ml) | 250 | 250 |
|  | $IC_{50}$ (ng/ml) | 190 | 221 |

Inhibition of Dermatophyte Growth

The compounds of the invention are also effective against dermatophytes. Testing was performed using a microdilution method based on the NCCLS M27A antifungal protocol. Compounds to be tested were prepared in DMSO and diluted to the appropriate concentration in RPMI 1640 medium (the dermatophyte growth medium). An inoculum of each test organism was prepared from oatmeal agar plates to contain $0.5–2.5 \times 10^3$ conidia/mL. One hundred microliters of the inoculum was added to each well of a 96-well microtiter plate containing 4 µL of a test compound and 96 µL of RPMI 1640. Terbinafine (sold under the brand name Lamisil®) was used as a positive control. Plates were incubated for four days at 35° C., and the MIC was determined by visual inspection. The data are summarized in the following table.

TABLE 5

|  | MIC (µg/mL) | | | |
|---|---|---|---|---|
| Organism | Compound 1 | Compound 3 | Compound 7 | Terbinafine |
| *T. rubrum* | 0.001 | 8.0 | 0.125 | 0.002 |
| *T. mentagrophytes* | 0.001 | 2.0 | 0.125 | 0.004 |
| *T. tonsurans* | 0.001 | 2.0 | 0.125 | 0.015 |
| *M. canis* | 0.001 | 2.0 | 0.125 | 0.015 |

Other Embodiments

From the above description, one skilled in the art can easily ascertain the essential characteristics of the present invention, and without departing from the spirit and scope thereof, can make various changes and modifications of the invention to adapt it to various usages and conditions. All publications and patents mentioned in this specification are incorporated by reference.

What is claimed is:

1. A substantially pure compound having the formula:

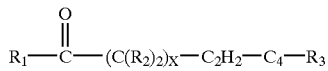

wherein —$C_2H_2$—$C_4$—$R_3$ is —CH=CH—C≡C—C≡C—$R_3$; $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

2. The compound of claim 1, wherein each $R_2$ is H.

3. The compound of claim 1, wherein each $R_2$ is, independently, H, $CH_3$, or $C_2H_5$.

4. The compound of claim 1, wherein the sum of the carbon atoms on the $R_2$ moieties is less than 15.

5. The compound of claim 4, wherein the sum of the carbon atoms on the $R_2$ moieties is less than 9.

6. The compound of claim 5, wherein the sum of the carbon atoms on the $R_2$ moieties is less than 5.

7. The compound of claim 1; wherein $R_3$ is a furan ring.

8. The compound of claim 1, wherein X is an integer between 5 and 7, inclusive.

9. The compound of claim 1, wherein the compound inhibits the growth of *Candida albicans*.

10. The compound of claim 8, wherein $R_3$ is a furan ring.

11. A pharmaceutical composition comprising a compound having the formula:

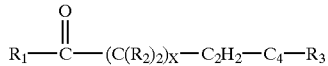

and a pharmaceutically acceptable carrier, wherein —$C_2H_2$—$C_4$—$R_3$ is —CH=CH—C≡C—C≡C—$R_3$; $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

12. A substantially pure compound having the formula:

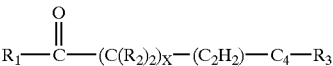

wherein —($C_2H_2$)—$C_4$—$R_3$ is —(CH=CH)—C≡C—C≡C—$R_3$; $R_1$ is OH, $NH_2$, $OCH_3$, or $OC_2H_5$, $R_3$ is a pyrrole, furan, or thiophene ring, and X is an integer between 5 and 7, inclusive.

13. The compound of claim 12, wherein $R_1$ is OH.

14. The compound of claim 12, wherein $R_3$ is a furan ring.

15. A method of inhibiting the growth of a fungal cell, said method comprising the step of contacting the cell with a cell-killing amount of a compound having the formula:

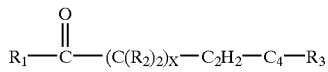

wherein —$C_2H_2$—$C_4$—$R_3$ is —CH=CH—C≡C—C≡C—$R_3$; $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

16. The method of claim 15, wherein each $R_2$ is H.

17. The method of claim 15, wherein each $R_2$ is, independently, H, $CH_3$, or $C_2H_5$.

18. The method of claim 15, wherein the sum of the carbon atoms on the $R_2$ moieties is less than 15.

19. The method of claim 18, wherein the sum of the carbon atoms on the $R_2$ moieties is less than 9.

20. The method of claim 19, wherein the sum of the carbon atoms on the $R_2$ moieties is less than 5.

21. The method of claim 15, wherein $R_3$ is a furan ring.

22. The method of claim 15, wherein X is an integer between 5 and 7, inclusive.

23. The method of claim 15, wherein the fungal cell is a *Candida albicans* cell.

24. The method of claim 23, wherein the compound inhibits growth of the *Candida albicans* cell by at least 90%.

25. A method of inhibiting the development of a fungal infection in an organism, said method comprising the step of contacting the organism with a compound having the formula:

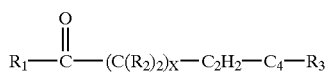

wherein —$C_2H_2$—$C_4$—$R_3$ is —CH=CH—C≡C—C≡C—$R_3$; $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

26. The method of claim 25, wherein the organism is a plant.

27. The method of claim 26, wherein the organism is an animal.

28. The method of claim 27, wherein the animal is a human.

29. A compound for treating a fungal infection, the compound having the formula:

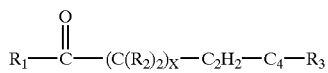

wherein —$C_2H_2$—$C_4$—$R_3$ is —CH=CH—C≡C—C≡C—$R_3$; $R_1$ is a hydroxyl group or a moiety that can be replaced by a hydroxyl group in a hydrolysis reaction; each $R_2$ is, independently, H or a monovalent hydrocarbon moiety containing between 1 and 4 carbon atoms, inclusive; $R_3$ is a pyrrole, furan, or thiophene ring; and X is an integer between 4 and 10, inclusive.

30. The compound of claim 29, wherein said fungal infection is caused by a dermatophyte.

* * * * *